(12) United States Patent
Yoshiba (10) Patent No.: US 11,992,395 B2
(45) Date of Patent: May 28, 2024

(54) METHOD FOR MANUFACTURING AN ABSORBENT ARTICLE

(71) Applicant: DAIO PAPER CORPORATION, Ehime (JP)

(72) Inventor: Megumi Yoshiba, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 927 days.

(21) Appl. No.: 16/980,687

(22) PCT Filed: Mar. 18, 2019

(86) PCT No.: PCT/JP2019/011096
§ 371 (c)(1),
(2) Date: Sep. 14, 2020

(87) PCT Pub. No.: WO2019/181831
PCT Pub. Date: Sep. 26, 2019

(65) Prior Publication Data
US 2021/0007909 A1   Jan. 14, 2021

(30) Foreign Application Priority Data
Mar. 19, 2018   (JP) .................................. 2018-050860

(51) Int. Cl.
*A61F 13/511* (2006.01)
*A61F 13/15* (2006.01)

(52) U.S. Cl.
CPC .. *A61F 13/51108* (2013.01); *A61F 13/15617* (2013.01); *A61F 2013/15878* (2013.01)

(58) Field of Classification Search
CPC .......... A61F 13/15617; A61F 13/15699; A61F 13/15731; A61F 13/51108; A61F 13/5116; A61F 2013/15878
See application file for complete search history.

(56) References Cited

U.S. PATENT DOCUMENTS

2005/0148971 A1* 7/2005 Kuroda ............. A61F 13/51121
604/385.04
2012/0321839 A1* 12/2012 Uematsu ........... A61F 13/15699
428/113
2017/0312144 A1   11/2017 Moritani

FOREIGN PATENT DOCUMENTS

EP   3437607   2/2019
JP   2007-143698   6/2007
(Continued)

OTHER PUBLICATIONS

International Search Report issued May 28, 2019 in International (PCT) Patent Application No. PCT/JP2019/011096.

*Primary Examiner* — Michele Kidwell
(74) *Attorney, Agent, or Firm* — Wenderoth, Lind & Ponack, L.L.P.

(57) ABSTRACT

An absorbent article comprising a top-surface sheet, a second sheet, and an absorber interposed between the top-surface sheet and the second sheet. The absorbent article allows a body fluid absorbed by the top-surface sheet to move to a non-skin side without deteriorating a soft touch feeling of cotton. The top-surface sheet 3 has a multi-layer structure including a non-heat fusible layer 10 made of a cellulose fiber and arranged on a skin side and a heat-fusible layer 11 made of a heat-fusible fiber and arranged on the non-skin side. The second sheet 6 made of a heat-fusible fiber is arranged on the non-skin side of the top-surface sheet 3. A large number of compressed parts 15 are formed on the non-skin side of the second sheet 6 by integrally recessing the second sheet 6 and the top-surface sheet 3 toward the skin side.

4 Claims, 6 Drawing Sheets

(56) References Cited

FOREIGN PATENT DOCUMENTS

| | | |
|---|---|---|
| JP | 2009-148328 | 7/2009 |
| JP | 2012-100785 | 5/2012 |
| JP | 2016-220986 | 12/2016 |
| JP | 2017-205143 | 11/2017 |

\* cited by examiner

METHOD FOR MANUFACTURING AN ABSORBENT ARTICLE

TECHNICAL FIELD

The present invention relates to an absorbent article to be used for an incontinence pad, a panty liner, a sanitary napkin, and the like, and in particular, an absorbent article in which joining strength between a top-surface sheet including cellulose fibers and a second sheet disposed on a non-skin side of the top-surface sheet is enhanced, and a method for manufacturing the absorbent article.

BACKGROUND ART

Conventionally, as absorbent articles for women, for example, incontinence pads, panty liners, and sanitary napkins, absorbent articles including an impermeable back-surface sheet such as a polyethylene sheet or a polyethylene sheet-laminated nonwoven fabric, a top-surface sheet, and an absorber made of paper cotton such as pulverized pulp interposed between the back-surface sheet and the top-surface sheet are known.

The top-surface sheet forms a skin-contact surface, and accordingly is required to be flexible, to be able to achieve a dry touch after absorption of an excreted liquid, to have little irritation to the skin, or the like. As materials that satisfy such requirements, nonwoven fabrics of synthetic fibers and resin mesh sheets are broadly employed in the field of absorbent articles. However, the top-surface sheet made of synthetic fibers was not sufficiently satisfactory in that it tended to cause itchiness, a rash, or the like.

In order to solve this problem, a top-surface sheet including a cotton fiber (a cotton fiber) as a raw material has been proposed. A top-surface sheet made of a cotton fiber has an advantage that a soft touch like underwear can be achieved. In absorbent articles, a top-surface sheet is desired to have high liquid permeability and to allow a liquid to rapidly move to the absorber. Meanwhile, there was a problem that when ordinary degreased cotton fiber is contained in the top-surface sheet, the top-surface sheet itself has high liquid retention property and a sticky feeling tends to remain on a surface.

In order to solve this problem, the following Patent Literature 1 discloses an absorbent article in which a top surface sheet is made of a cotton nonwoven fabric, and a heat-fusible fiber sheet, which is a lower layer of the top surface, having a lower fiber density than that of the cotton nonwoven fabric and having hydrophilicity is interposed between the top surface sheet and an absorber, and in such a laminated state, a large number of embossments from a top surface side are formed.

Furthermore, the following Patent Literature 2 discloses an absorbent article in which a top-surface sheet is a nonwoven fabric made of at least two fiber layers including a first fiber layer made of cotton and thermoplastic resin fibers and a second fiber layer made of hydrophobic thermoplastic resin fibers; the nonwoven fabric has a first surface being a skin-facing side surface and formed of the second fiber layer, and a second surface being a non-skin-facing side surface and facing the absorber; the nonwoven fabric is provided with a plurality of protrusions protruding toward the first surface, and a plurality of recesses provided between adjacent protrusions and recessed toward the second surface, each of the protrusions having a gap faced by the second surface of the nonwoven fabric.

CITATION LIST

Patent Literature

Patent Literature 1: JP No. 2009-148328
Patent Literature 2: JP No. 2016-220986

SUMMARY OF INVENTION

Technical Problem

However, in the absorbent article described in the above Patent Literature 1, since embossing is performed by compression from a top-surface side, that is, an outer surface side of the cotton nonwoven fabric facing the skin surface, in embossing processing, a non-heat fusible cotton nonwoven fabric is interposed between tip ends of emboss protrusions provided to an embossing roll and a heat-fusible fiber layer. Consequently, there is a problem that heat at the tip ends of the emboss protrusions is not sufficiently transferred to the heat-fusible fiber, joining strength between a second sheet arranged on the non-skin side of the top-surface sheet and the top surface sheet tends to become lower, and a body fluid does not easily move from the top-surface sheet to the second sheet.

Furthermore, when a process for providing recesses and protrusions with heating is performed to the cotton nonwoven fabric, entanglement of fibers by, for example, hydroentanglement of the cotton nonwoven fabric may be released, and the fiber ends may come out, or the cotton nonwoven fabric may be broken. Consequently, there were problems of deterioration of a touch feeling due to damage of the smoothness of the surface and reduction of strength.

On the other hand, in the absorbent article described in the above Patent Literature 2, since a layer including cotton is disposed on a non-skin-facing surface side of the top-surface sheet, which is not brought into direct contact with the skin, it is not possible to make use of a soft touch feeling of cotton.

Thus, a main object of the present invention is to provide an absorbent article capable of allowing a body fluid absorbed by a top-surface sheet to move to a non-skin side without deteriorating a soft touch feeling of cotton.

Solution to Problem

In order to solve the above problem, as the present invention according to claim 1, an absorbent article is provided. The absorbent article includes a top-surface sheet and a back-surface sheet with an absorber interposed therebetween. The top-surface sheet includes a non-heat fusible layer arranged on a skin side and made of a cellulose fiber, and a heat-fusible layer arranged on a non-skin side and made of a heat-fusible fiber. A second sheet made of a heat-fusible fiber is arranged on the non-skin side of the top-surface sheet, and a large number of compressed parts are formed on a non-skin side surface of the second sheet by integrally recessing the second sheet and the top-surface sheet toward the skin side.

In the invention described in claim 1 above, since the non-heat fusible layer made of a cellulose fiber is arranged on the skin-contact surface of the top-surface sheet, a soft touch feeling of the cellulose fiber (for example, a cotton fiber) can be obtained. Furthermore, the top-surface sheet has a laminate structure including the non-heat fusible layer on the skin side and the heat-fusible layer on the non-skin side, and in a state in which the second sheet made of a heat-fusible fiber is arranged on the non-skin side of the top-surface sheet, a large number of compressed parts are formed in the non-skin side surface of the second sheet by integrally recessing the second sheet and the top-surface sheet toward the skin side. Accordingly, the heat-fusible second sheet and the heat-fusible layer (non-skin side layer) of the top-surface sheet are firmly joined to each other by the compressed parts, and a body fluid easily moves from the top-surface sheet to the second sheet disposed on the lower layer side of the top-surface sheet. Furthermore, since the compressed part heat-fuses the second sheet and the heat-fusible layer constituting the non-skin side layer of the top-surface sheet by compression from the non-skin side of the top-surface sheet, the non-heat fusible layer made of a cellulose fiber on the skin side is not compressed with heated at high temperature, a nonwoven fabric can be prevented from being broken when entanglement of the fibers of the non-heat fusible layer is released due to heating or compression, the smoothness of the surface can be maintained, and deterioration of the touch and reduction of the strength can also be prevented.

The invention described in claim 2 provides the absorbent article according to claim 1, wherein the non-heat fusible layer and the heat-fusible layer are joined to each other in a state in which fibers of the non-heat fusible layer and fibers of the heat-fusible layer are entangled with each other.

In the invention described in claim 2 above, it is preferable that the non-heat fusible layer and the heat-fusible layer are joined to each other by entangling the fibers of each layer by, for example, hydroentanglement. This has advantages that it is possible to prevent inhibition of movement of a body fluid due to adhesives, which occurs when joining is performed using adhesives; a body fluid easily moves from the non-heat fusible layer to the heat-fusible layer via fibers entangled with each other; and since the joining strength is not so strong, the effect of heating or compression on the non-heat fusible layer is reduced when the heat-fusible layer is heated and compressed.

The invention described in claim 3 provides the absorbent article according to claim 1 or 2, wherein the second sheet is formed at a lower basis weight and in a lower density than the heat-fusible layer.

In the invention described in claim 3 above, the second sheet is formed at a lower basis weight and in a lower density than the heat-fusible layer of the top-surface sheet, thereby strengthening joining between the second sheet and the heat-fusible layer by the compressed parts.

The invention described in claim 4 provides the absorbent article according to any one of claims 1 to 3, wherein a large number of the compressed parts are formed in an intermittent pattern in which the compressed parts are disposed at intervals.

In the invention described in claim 4 above, when the pattern of the compressed parts is an intermittent pattern in which a large number of the compressed parts are disposed at intervals, an entire area of the compressed parts can be reduced, touch (smoothness) of the non-heat fusible layer or strength can be reliably maintained.

The invention described in claim 5 provides the absorbent article according to any one of claims 1 to 4, wherein the non-heat fusible layer is formed of 100% by weight of cotton fibers.

In the invention described in claim 5 above, by forming the non-heat fusible layer of 100% by weight of cotton fibers, flexibility or feeling property of the top-surface sheet becomes particularly excellent.

The invention described in claim 6 provides the absorbent article according to any one of claims 1 to 5, wherein the heat-fusible layer does not include a non-heat fusible fiber.

In the invention described in claim 6 above, in order to strengthen the joining strength between the heat-fusible layer and the second sheet, the heat-fusible layer has a configuration not including the non-heat fusible fibers such as cellulose fibers.

The invention described in claim 7 provides a method for manufacturing the absorbent article according to any one of claims 1 to 6. The method includes allowing a laminate of the top-surface sheet and the second sheet to pass between a flat roll and a convex roll, the flat roll having a flat surface and not being heated, and the convex roll having a surface formed with a large number of protrusions corresponding to the compressed parts and being heated at least at a time of compression, thereby heat-fusing and joining the second sheet and the heat-fusible fiber of the heat-fusible layer to each other while forming the compressed parts.

The invention described in claim 7 above is a first manufacturing method for forming the compressed parts. The method allows the top-surface sheet and the second sheet in a laminated state to pass between the flat roll and the convex roll. Thus, a laminate of the top-surface sheet and the second sheet, in which a surface is flat and excellent in a touch feeling, and the heat-fusible layer of the top-surface sheet and the second sheet are firmly joined in the compressed parts.

The invention described in claim 8 provides a method for manufacturing the absorbent article according to any one of claims 1 to 6. The method includes allowing the top-surface sheet to pass between a flat roll and a convex roll, the flat roll having a flat surface and not being heated, and the convex roll having a surface formed with a large number of protrusions and being heated at least at a time of compression to form a large number of intermediate compressed parts in a non-skin side surface of the top-surface sheet by integrally recessing the heat-fusible layer and the non-heat fusible layer toward a skin side, and then allowing the top-surface sheet to pass between a second flat roll and a second convex roll, the second flat roll having a flat surface and not being heated, and the second convex roll having a surface formed with a large number of protrusions corresponding to the compressed parts and being heated at least at compression time, thereby heat-fusing and joining the second sheet and the heat-fusible fiber of the heat-fusible layer while forming the compressed parts.

In the invention described in claim 8 above, by forming the intermediate compressed parts in the top-surface sheet in advance, joining strength between the non-heat fusible layer and the heat-fusible layer is enhanced. Then, the top-surface sheet and the second sheet in a laminated state are allowed to pass between the flat roll and the convex roll.

Advantageous Effect of Invention

As described above in detail, the present invention makes it possible to provide an absorbent article capable of allowing a body fluid absorbed by a top-surface sheet to move to a non-skin side without deteriorating a soft touch feeling of cotton.

DESCRIPTION OF EMBODIMENTS

Figure 1:
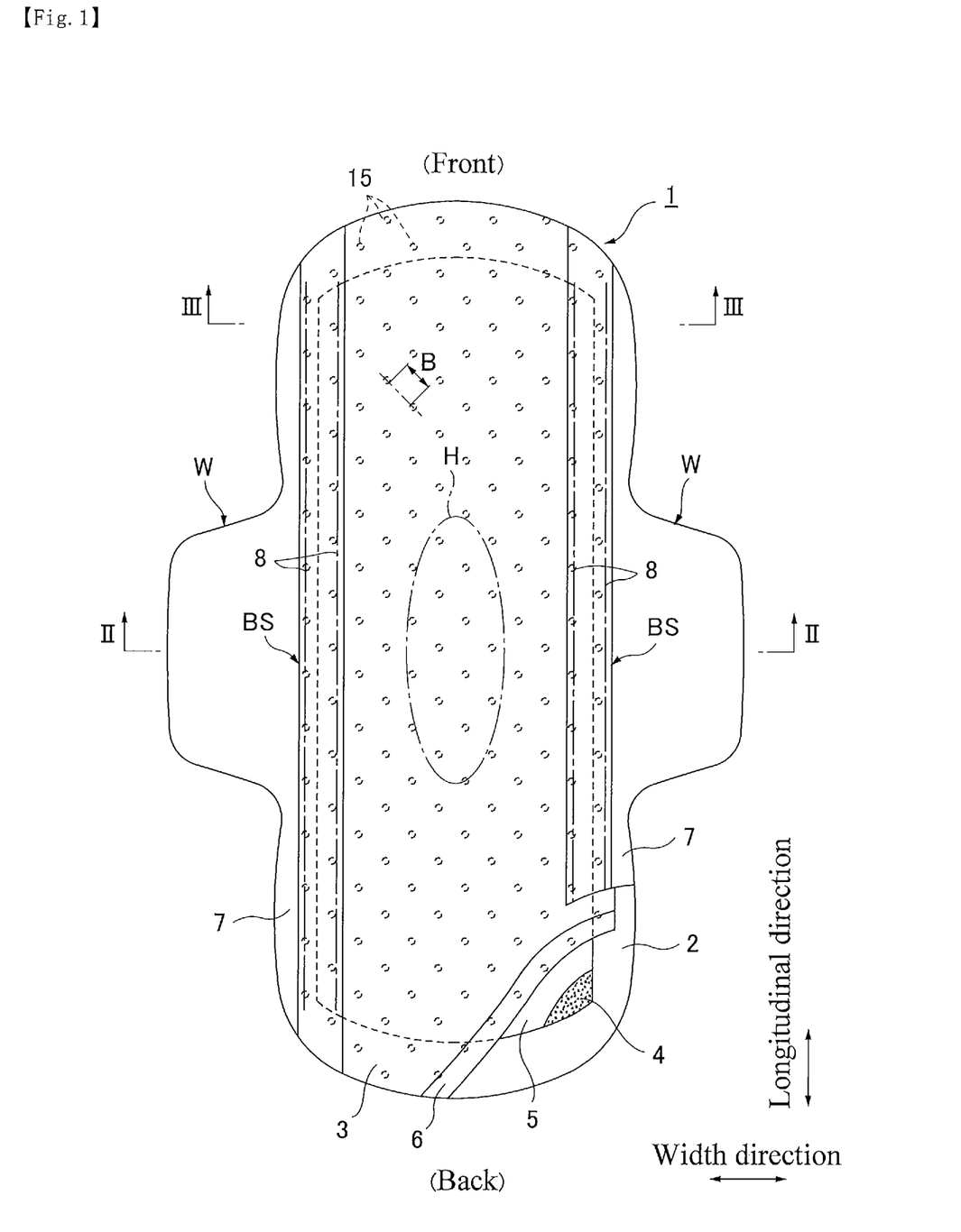
FIG. 1 is a partially broken development view of a sanitary napkin 1 according to the present invention.
Figure 2:
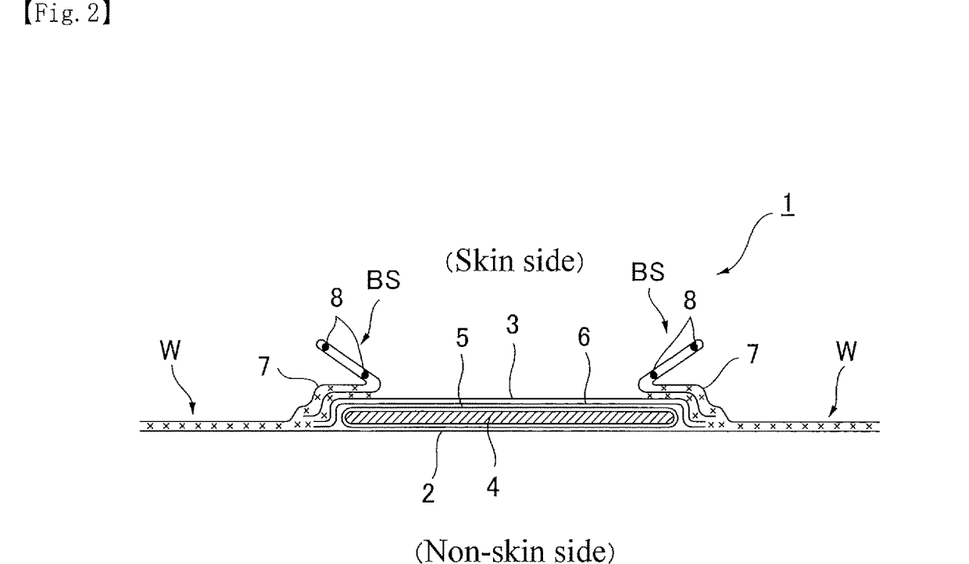
FIG. 2 is an arrow view taken along line II-II in FIG. 1.
Figure 3:
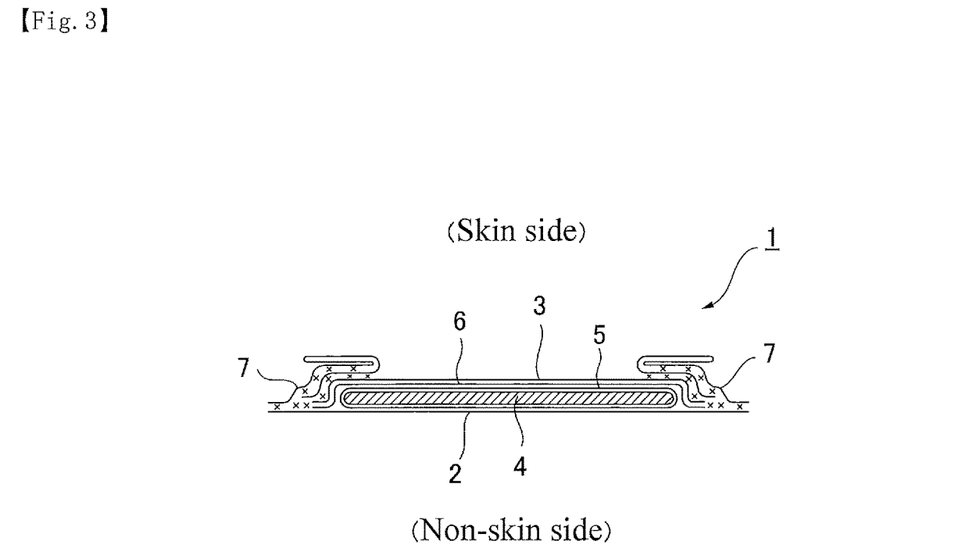
FIG. 3 is an arrow view taken along line III-III in FIG. 1.

Hereinafter, an embodiment of the present invention will be described in detail with reference to the drawings.
<One Example of Basic Structure of Sanitary Napkin>
A sanitary napkin 1 according to the present invention mainly includes, as shown in FIGS. 1 to 3, an impermeable back-surface sheet 2 made of, for example, a polyethylene sheet; a top-surface sheet 3 forming a skin-contact surface and allowing rapid permeation of a body fluid; an absorber 4 interposed between both sheets 2 and 3 and made of cotton pulp, synthetic pulp, or the like; an encapsulating sheet 5 covering at least a skin-side surface and a non-skin side surface of the absorber 4 for shape retention and improvement of diffusivity of this absorber 4 and made of a crepe paper, a nonwoven fabric, or the like; a second sheet 6 interposed between the top-surface sheet 3 and the absorber 4; and a side non-woven fabric 7,7 forming a pair of right and left three-dimensional gathers BS, BS provided to protrude with a substantial lateral edge part of the absorber 4 as a rise-up base edge to a skin side within a predetermined section in the front-back direction so as to include at least a body fluid discharge portion H of a wearer. In the surrounding of the absorber 4, at upper and lower end edge parts thereof, outer edge parts of the back-surface sheet 2 and the top-surface sheet 3 are joined by an adhesive such as a hot melt or by joining means such as a heat seal and an ultrasonic wave seal. Furthermore, at both lateral edge parts thereof, the back-surface sheet 2 extending further to the lateral side than the absorber 4 and a side non-woven fabric 7 are joined with an adhesive such as a hot melt or by joining means such as a heat seal, and an ultrasonic wave seal. In an example shown in the drawings, the absorber 4 has a single-layer structure but may have a multi-layered structure forming a middle-height portion, and also may have a multi-layered structure in which absorbers having the same size and shape are stacked.

For the back-surface sheet 2, a sheet material having at least water-blocking properties, for example, polyethylene, is used. In recent years, however, from the viewpoint of preventing a moist stuffy feeling, a sheet material having moisture permeability has tended to be used. As the water-blocking and moisture-permeable sheet material, a microporous sheet obtained by molding a sheet by melting and kneading an inorganic filler in an olefin-based resin such as polyethylene or polypropylene, followed by stretching in uniaxial or biaxial direction is suitably used. On an unused surface side (outside surface) of the back-surface sheet 2, one or a plurality of stripes of sticking layers (not shown in the drawing) is formed, so that the sanitary napkin 1 is fixed to underwear when wearing on the body. As the back-surface sheet 2, a poly-laminated nonwoven fabric in which a plastic film and a nonwoven fabric are laminated may be used.

The absorber 4 can absorb and retain the body fluid, and the one in which a particulate superabsorbent polymer is dispersed and mixed in fluffy pulp fiber, or a polymer sheet including the superabsorbent polymer interposed in a predetermined region between the upper layer sheet disposed on the skin side and the lower layer sheet disposed on a non-skin side can be used.

Examples of the pulp fiber include one made of cellulose fibers such as chemical pulp obtained from timber or molten pulp, and artificial cellulose fibers such as rayon and acetate. From the viewpoint of function and price, one made of softwood pulp having a fiber length longer than hardwood pulp is suitably used. The basis weight of the pulp fiber is set at 150 to 500 $g/m^2$, and preferably 250 to 400 $g/m^2$. The basis weight of the superabsorbent polymer is set at 70 to 470 $g/m^2$, and preferably 140 to 240 $g/m^2$.

Examples of the superabsorbent polymer include crosslinked polyacrylate, self-crosslinked polyacrylate, a saponified product of a crosslinked product of an acrylic acid ester-vinyl acetate copolymer, a crosslinked product of an isobutylene/maleic anhydride copolymer, a crosslinked product of polysulfonate, and a partially crosslinked water-swelling polymer such as polyethylene oxide or polyacrylamide. Among these examples, acrylic acid or acrylate salt-based being excellent in absorption amount and water absorption speed is suitable. In the manufacturing process, an absorption ratio (water absorption power) and an absorption speed of the superabsorbent polymer having absorbing performance may be adjusted by adjusting crosslink density and crosslink density gradient.

In the example shown in the drawings, the top-surface sheet 3 is formed in a width to an extent that the top-surface sheet 3 has a width slightly larger than a width of the absorber 4 and only covers the absorber 4. The outside in the width direction of the top-surface sheet 3 is covered with the side nonwoven fabric 7 (a member other than the top-surface sheet 3) extending from surfaces of both side part surfaces of the top-surface sheet 3. A part on a center side in the width direction of the side nonwoven fabric 7 forms a three-dimensional gather BS. As the side nonwoven fabric 7, depending on objectives such as prevention of permeation of a body fluid or enhancement of a touch feeling, a nonwoven fabric material, to which appropriate water repelling treatment or hydrophilic treatment is applied, can be preferably used. As such side nonwoven fabric 7, one formed by an appropriate processing method using a natural fiber, a synthetic fiber or a recycled fiber as a raw material can be used. However, in order to eliminate a stiff feeling and to prevent a moist stuffy feeling, a nonwoven fabric having aeration properties with the basis weight reduced is preferable. Specifically, a nonwoven fabric produced by setting the basis weight at 15 to 23 $g/m^2$ is desirably used, and in order to securely prevent permeation of the body fluid, a water-repellent nonwoven fabric coated with a water repellent agent, such as a silicon-based or paraffin-based water repellent agent, or the like, is suitably used.

As shown in FIGS. 2 and 3, the side nonwoven fabric 7 adhesively bonds to an outer side portion of a middle portion in a width direction with an adhesive such as a hot melt over a range from an inside position of the absorber 4 to an outer peripheral edge of the back-surface sheet 2 slightly exceeding an absorber side edge.

On the other hand, an inner side portion of the side nonwoven fabric 7 is folded substantially into two and in the inside of the two-folded sheet, one or a plurality of thread-like elastic stretchable members, two thread-like elastic stretchable members 8, 8 in the example shown in the drawings, in which both ends or an appropriate position in the longitudinal direction is fixed to the middle portion in the height direction of the two-folded sheet, are arranged in a state in which both ends or an appropriate position in the longitudinal direction is fixed. The two-folded sheet parts, in the front and back end parts, are fixed to a top-surface sheet 3 side in a folded state as shown in FIG. 3

<Top-Surface Sheet>

Figure 4:
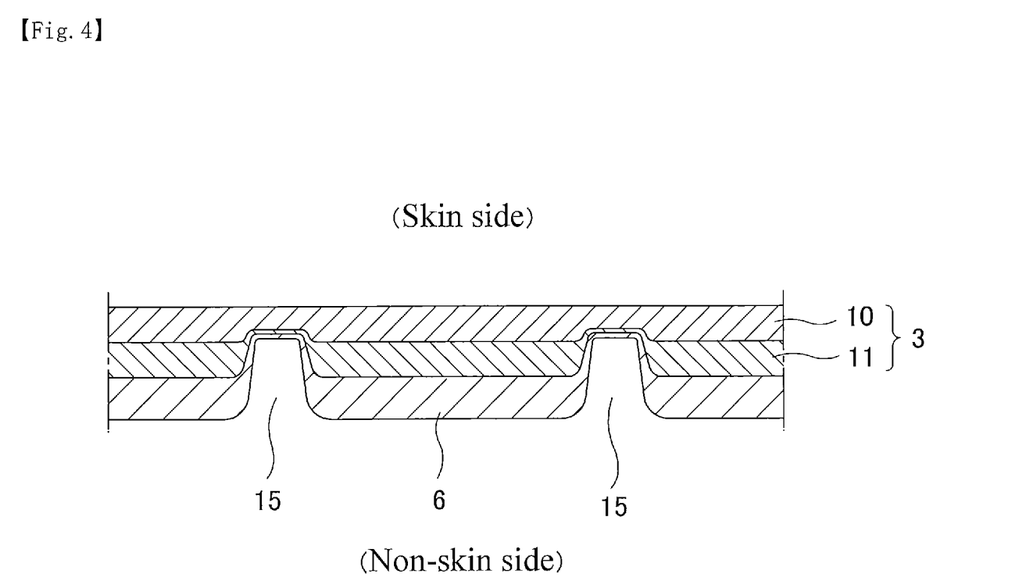
FIG. 4 is an enlarged sectional view of a top-surface sheet 3 and a second sheet 6 in the vicinity of compressed parts 15.

A top-surface sheet 3 forms a skin-contact surface that is a part covering a skin side of the absorber 4. As shown in FIG. 4, the top-surface sheet 3 has a multi-layer structure including a non-heat fusible layer 10 arranged on the skin side and made of a cellulose fiber, and a heat-fusible layer 11 arranged on the non-skin side and made of a heat-fusible fiber. The top-surface sheet 3 desirably has a two-layer structure of the non-heat fusible layer 10 and the heat-fusible layer 11, but may be provided in the middle portion thereof with a middle layer made of a cellulose fiber, a synthetic fiber, or the like.

The non-heat fusible layer 10 forming the skin-contact surface of the top-surface sheet 3 is made of a nonwoven fabric containing hydrophilic cellulose fibers. Examples of the hydrophilic cellulose fibers include naturally derived fibers such as a cotton fiber (a cotton fiber) and a pulp fiber, and artificial cellulose fibers such as a rayon fiber, an acetate fiber, and a Lyocell fiber. As the cotton fiber, any cotton fibers can be used, and examples thereof include raw cotton of cotton, refined/bleached cotton fiber or dyed cotton fiber after refining/bleaching, refined/bleached and degreased cotton fiber, and further, recovered wool obtained by fibrillating one that was formed into thread or cloth. In order to enhance absorption speed and diffusivity of liquid by a sheet in the lower layer side, in particular, a degreased cotton fiber in which natural fat and oil such as cotton wax attached to the surface of the cotton fiber has been degreased is preferably used.

The non-heat fusible layer 10 is desirably made of a spunlace nonwoven fabric made of 100% by weight of cotton fiber. When only a cotton fiber is included, it is possible that a soft touch is obtained, and skin trouble such as itchiness or the rash during wearing does not easily occur even when wearing for a long time. Furthermore, the spunlace nonwoven fabric has advantages, for example, not using adhesives, having flexibility, and the like.

The basis weight of the non-heat fusible layer 10 may be 10 to 30 g/m$^2$ and preferably 10 to 15 g/m$^2$ so that the flexibility and the feeling of cellulose fibers can be exhibited. The basis weight of the nonwoven fabric is obtained by cutting out a test sample having a dimension of 50 mm×50 mm (±2 mm), measuring the weight of the test sample, and converting it into the weight per 1 m$^2$. When there are a large number of openings in a partial region of the nonwoven fabric, measurement of a region of a nonwoven fabric not having openings is performed. Furthermore, when a large number of openings are formed in an entire surface of the nonwoven fabric, a large number of parts each of which does not include openings are cut out. Then, a total weight of the large number of cut-out parts is measured such that a total area of the large number of cut-out parts becomes 2500 mm$^2$, and the total area is divided by the total area so that the basis weight can be obtained.

As the heat-fusible layer 11 forming a non-skin-contact surface of the top-surface sheet 3, a porous or a non-porous nonwoven fabric is used. As a fiber raw material of the nonwoven fabric, a synthetic fiber is contained. Examples thereof may include thermoplastic synthetic fibers such as olefin-based fibers such as polyethylene or polypropylene, polyester-based fibers, polyamide-based fibers, and, in addition to these synthetic fibers, recycled fibers such as rayon or cupra, and natural fibers such as cotton. As the nonwoven fabric, a non-woven fabric obtained by appropriate processing methods such as a spun lace method, a spun bond method, a thermal bond method, a melt-blown method, and a needle punch method can be used. Among these processing methods, the spun lace method is excellent in rich flexibility, and a drape property, and the thermal bond method is excellent in bulkiness and compression restorability. When the heat-fusible layer 11 is made of a nonwoven fabric containing a synthetic fiber, a joining property can be enhanced by thermal melting of heat-fusible fiber, the heat-fusible layer 11 does not easily retain liquid, liquid permeability toward a lower layer side becomes preferable, and it is possible that a phenomenon that a body fluid is retained in heat-fusible layer 11 and returns reversely to a skin side does not easily occur.

It is preferable that the heat-fusible layer 11 does not include a non-heat fusible fiber, specifically, the cellulose fibers described above, and that the heat-fusible layer 11 includes only a heat-fusible fiber, specifically, a synthetic fiber. As described in detail later, the heat-fusible layer 11 is heat-fused to a second sheet 6 on the lower layer side in the compressed part 15. Therefore, if heat-fusible layer 11 includes a non-heat fusible fiber, the heat-fusible layer 11 is not easily heat-fused in the compressed part 15. As a result, joining strength between the heat-fusible layer 11 and the second sheet 6 may be deteriorated.

The basis weight of the heat-fusible layer 11 is preferably larger than that of the non-heat fusible layer 10, and specifically, the basis weight is 10 to 40 g/m$^2$, and preferably 15 to 20 g/m$^2$. When the basis weight of the heat-fusible layer 11 is larger than that of the non-heat fusible layer 10, less effect is given on the non-heat fusible layer 10 in compression with heating of the second sheet 6 and the heat-fusible layer 11.

The non-heat fusible layer 10 and the heat-fusible layer 11 are desirably joined to each other by a predetermined joining method. It is not preferable that the layers 10 are 11 are provided in a state in which they are not joined but just laminated, because strength of the non-heat fusible layer 10 made of cellulose fiber becomes weak and is easily broken. In other words, it is preferable that the non-heat fusible layer 10 is joined to the heat-fusible layer 11 because the non-heat fusible layer 10 is reinforced by the heat-fusible layer 11, and breakage of the top-surface sheet 3 can be prevented. Furthermore, when the top-surface sheet has the same basis weight, it is preferable that the non-heat fusible layer 10 and the heat-fusible layer 11 form a laminate structure also from the viewpoint that a laminate structure of the non-heat fusible layer 10 and the heat-fusible layer 11 permits reduction of the use amount of cellulose fibers being more expensive than synthetic fibers, so that the cost of the top-surface sheet 3 can be suppressed as compared with the case where only the non-heat fusible layer 10 is included.

The non-heat fusible layer 10 and the heat-fusible layer 11 are joined preferably by entangling fibers with each other instead of using adhesive or the like. When joining is performed by entangling these fibers with each other, as compared with a case where joining is performed using adhesives or the like, a member such as adhesives, easily preventing a body fluid from moving, is not interposed between the non-heat fusible layer 10 and the heat-fusible layer 11. Therefore, the body fluid easily moves from the non-heat fusible layer 10 to the heat-fusible layer 11, and the body fluid easily moves from the non-heat fusible layer 10 to the heat-fusible layer 11 via entangled fibers. Furthermore, joining by entanglement of fibers also has advantages that since joining strength does not become so strong, the effect of heating and compression on the non-heat fusible layer 10 can be reduced when the heat-fusible layer 11 is heated and compressed. Examples of the joining method by entangling fibers include a hydroentanglement process of jetting of a high-pressure water stream to entangle fibers, a punching method of mechanically entangling fibers by needle punching, and the like.

Figure 5:
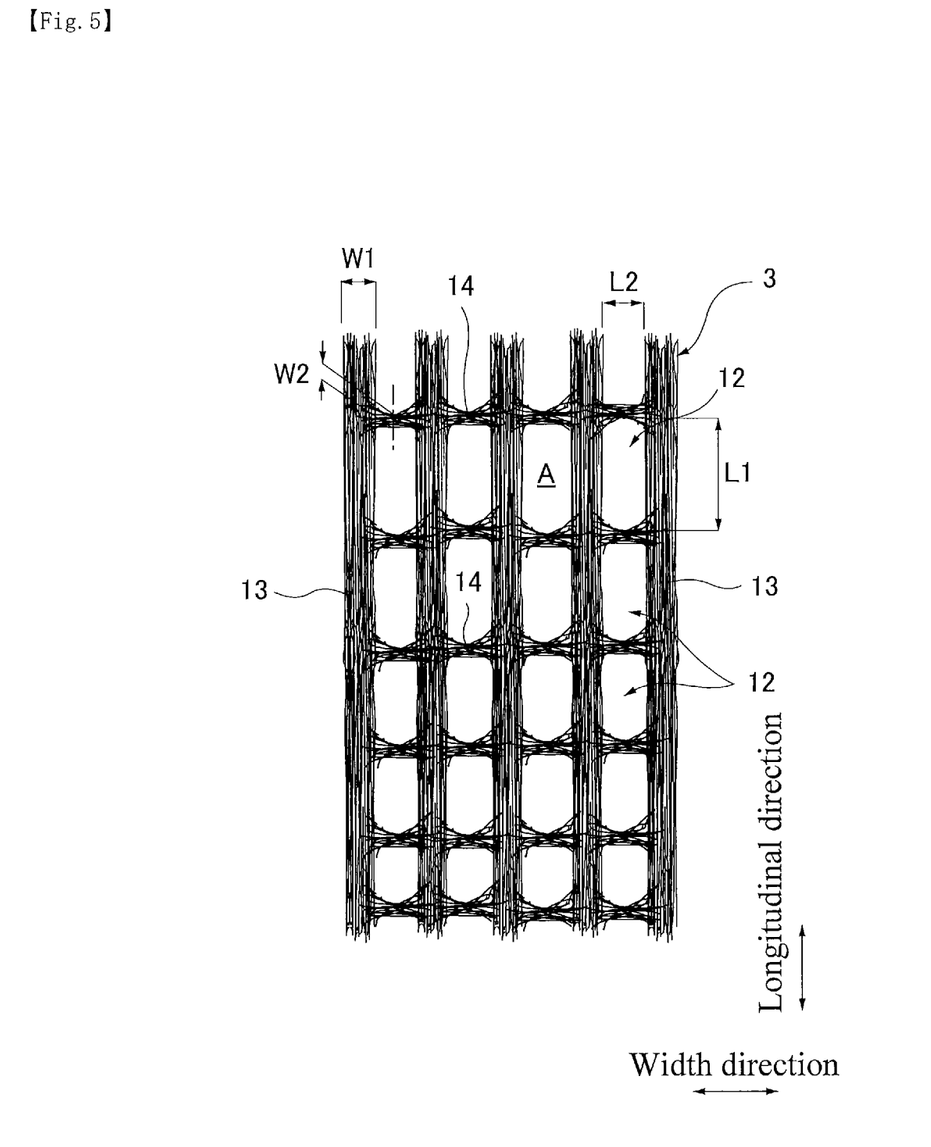
FIG. 5 is an enlarged plan view of the top-surface sheet 3.

By the way, as shown in FIG. 5, at least the non-heat fusible layer 10 of the top-surface sheet 3 is preferably provided with a large number of openings 12, 12 . . . penetrating from the top surface to the back surface at least in a region corresponding to a body fluid discharge portion H so as to enhance liquid permeability. Specifically, the openings 12 may be formed by supporting a fiber material on a mesh-like support in a hydroentanglement process at the time of manufacturing spunlace. In this case, by changing a condition of the mesh to be used, it is possible to adjust a size of each opening and an opening rate. Of course, the openings may be formed by performing punching (die cutting) on a nonwoven fabric after manufacture. The openings 12 may be provided on the entire surface sheet, but is preferably provided at least in the region corresponding to the body fluid discharge portion H. Preferably, the openings 12 are provided in a region of 15% or more of the absorber length in a product length direction and 50% or more of the absorber width in a product width direction including the region corresponding to the body fluid discharge portion H, more preferably in a region of 50% or more of the absorber length in the product length direction and 70% or more of the absorber width in the product width direction including the region corresponding to the body fluid discharge portion H. When the formation region of the openings 12 is less than 15% of the absorber length in the product length direction and less than 50% of the absorber width in the product width direction, a body fluid discharge range may not be able to be covered, a body fluid remains on the surface sheet 3, a sticky feeling is felt, and skin trouble such as itchiness or the rash during wearing easily occurs. The opening 12 may be provided to only the non-heat fusible layer 10, or provided to both the non-heat fusible layer 10 and the heat-fusible layer 11.

As shown in FIG. 5, the opening 12 is formed in a vertically long shape being long in the longitudinal direction of the sanitary napkin 1. For this reason, a liquid easily permeates therethrough as compared with a circular opening, so that the body fluid easily passes through the surface sheet 3 via the opening 12, and water retention in the surface sheet 3 is reduced. Furthermore, when the body fluid passes through the opening 12, a liquid passes through while being deformed to be vertically long. Accordingly, a diffusion direction of the body fluid may be controlled in the longitudinal direction of the napkin, diffusion in a lateral direction is suppressed, and lateral leakage rarely occurs. Note here that in the case of the spunlace, although shapes of the openings tend to be non-uniform, the shape of the opening 12 becomes a shape such as an approximately rectangular shape, a corner-eliminated elongated opening shape, or an elliptical shape.

As dimensions of the opening 12, it is preferable that a length L1 of the sanitary napkin 1 in the longitudinal direction is 1.0 to 4.0 mm, preferably 1.5 to 3.0 mm, and a length L2 of the sanitary napkin 1 in the width direction is 0.5 to 1.5 mm, preferably 0.5 to 1.0 mm. When a dimension of the opening 12 is less than 0.5 mm, a body fluid hardly passes through, and it is difficult to form a clear opening due to fluffing of the fiber. When a maximum dimension of the opening 12 exceeds 4.0 mm, a liquid from the opening 12 flows back, which causes surface exposure of a constituent material of the absorber 4. Furthermore, it is preferable that a ratio (L1/L2) of L1 to L2 is set to 1.2 to 5.0, preferably 2.0 to 3.0. It is preferable that an area A of the opening 12 is set to 0.9 to 3.0 $mm^2$, and preferably 0.9 to 2.5 $mm^2$. Further, it is preferable that the opening rate is set to 15 to 45%, preferably 17 to 30%, more preferably 18 to 25%. The dimensions of the opening 12 may not be uniform over the entire part, and may be formed in an arbitrary size as long as the size falls within the above-mentioned range.

As shown in FIG. 5, preferably, at least the non-heat fusible layer 10 of the top-surface sheet 3 has a structure of the cotton fiber in which a large number of vertical stripes 13, 13, . . . extending along the longitudinal direction of the sanitary napkin 1 and formed at an interval in the width direction, a plurality of horizontal stripes 14, 14, . . . extending along the width direction of the sanitary napkin 1, and linking the adjacent vertical stripes 13, 13, . . . formed at an interval in the longitudinal direction are formed, and the openings 13 are formed in parts surrounded by the vertical stripe 13 and the horizontal stripe 14.

It is preferable that a width W1 of the vertical stripe 13 is set to 0.5 to 2.5 mm, and preferably 0.8 to 2.3 mm, and a width W2 of the horizontal stripe 14 is set to 0.2 to 1.6 mm, and preferably 0.3 to 1.4 mm. Furthermore, it is preferable that a ratio (W1/W2) of the width W1 to the width W2 is set to 1.2 to 2.0, and preferably 1.5 to 2.0. When the width W1 of the vertical stripe 13 is set to be larger than the width W2 of the horizontal stripe 14, liquid diffusion in the longitudinal direction of the sanitary napkin 1 along the vertical stripe 13 is likely to occur.

The vertical stripe 13 is formed to have a larger fiber amount and higher density as compared with the horizontal stripe 14. Thus, only a part of the vertical stripe 13 comes into contact with the skin, a contact area to the skin is reduced, and therefore, occurrence of skin trouble such as itchiness or the rash during wearing may be suppressed after wearing for a long time. At the same time, a sticky feeling is reduced even after liquid discharge. Furthermore, when a body fluid passes through the surface sheet 3, diffusion in the longitudinal direction of the sanitary napkin 1 along the vertical stripe 13 having relatively high density is likely to occur by the capillary phenomenon of the fiber. In addition, since a diffusion direction of a body fluid passing through the opening 12 and a diffusion direction of a body fluid permeating through the surface sheet 3 coincide with each other in the longitudinal direction of the sanitary napkin 1, penetration into the vertical stripe 13 of the surface sheet 3 occurs by being drawn into a body fluid passing through the opening 12. Thus, liquid remaining of the surface sheet 3 is suppressed as much as possible.

Measurement of the fiber amount can be performed according to "Method of screening test of paper pulp" defined in JIS P8207: 2009. Furthermore, measurement of the density can be performed by automatically measuring a thickness $T_0$ (load: 0.5 $gf/cm^2$) using an automatic measurement device (Handy Compression Tester, KES-G5, manufactured by KATO TECH CO., LTD.) and calculating from the basis weight/$T_0$.

It is preferable that a water repellent agent is externally added and applied to at least the non-heat fusible layer 10 of the top-surface sheet 3 in at least a region corresponding to the body fluid discharge portion H. As the water repellent agent, it is possible to appropriately select and use a water repellent agent less irritating to the skin among known water repellent agents such as a paraffin-based and a silicone-based water repellent agent, and it is more preferable to appropriately select and use oil and fat less irritating to the skin, for example, glyceryl stearate, stearic acid amide, zinc stearate, calcium stearate, diethanol amide stearate, and magnesium stearate. Among these materials, glyceryl stearate is particularly preferable. When a water repellent agent made of glyceryl stearate is used in the sanitary napkin 1, an application amount thereof is preferably set to 0.05 to 1.50 parts by weight with respect to 100 parts by weight of the fibers (in the case of double-sided application, a total application amount of both sides). A more preferable application amount is 0.03 to 1.50 parts by weight. When the application amount of the water repellent agent is less than 0.05 parts by weight, a water repellent effect may be insufficient in some cases. When the application amount exceeds 1.50 parts by weight, the water repellency is excessively high, and moisture is rather difficult to permeate.

The water repellent agent may be applied only to the skin-contact surface or both the skin-contact surface and the surface on the absorber 4 side. However, it is preferable that at least a water absorption amount obtained from a water absorption amount test described below is 0.03 g or less, and suitably 0.02 g or less.

A water absorption amount of the surface sheet 3 is obtained according to the following procedure. (1) A sample of 10 cm square is prepared, and a weight thereof is measured (A). (2) Three paper filters of 10 cm square are stacked such that a smooth side faces upward, and the sample is set thereon. (3) Onto the set sample, 3 ml of room temperature tap water is dropped, and left for five minutes. (4) A weight of the sample after being left for five minutes is measured (B). (5) The absorption amount (water retention amount) of the surface sheet 3 is obtained from (B)−(A)=absorption amount (g).

Known methods such as transfer, spraying, brush coating, impregnation, and dipping can be appropriately used as a coating method for the water repellent agent. In the case of imparting a difference in water absorbency on both sides of the sheet, a coating method by transfer can be preferably used.

The water repellent agent is preferably applied on the entire surface from the viewpoint of manufacturing efficiency. However, it is sufficient that the water repellent agent may be applied only to at least a region corresponding to body fluid discharge portion H or a part receiving the excreted liquid.

<Second Sheet>

The second sheet 6 is arranged between the top-surface sheet 3 and the absorber 4, and adjacent to a non-skin side of the top-surface sheet 3. In other words, a non-skin side surface of the heat-fusible layer 11 constituting a non-skin side layer of the top-surface sheet 3 and a skin-side surface of the second sheet 6 are arranged facing each other. It is preferable that the second sheet 6 has substantially the same planar shape as that of the top-surface sheet 3. As mentioned below, this second sheet 6 is joined to the heat-fusible layer 11 of the liquid-permeable top-surface sheet 3 by thermal fusion, in compressed part 15.

As the second sheet 6, a porous or non-porous nonwoven fabric is used similar to heat-fusible layer 11 of the top-surface sheet 3. As a fiber raw material of the nonwoven fabric, a synthetic fiber is contained. Examples thereof may include thermoplastic synthetic fibers such as olefin-based fibers such as polyethylene or polypropylene, polyester-based fibers, polyamide-based fibers, and, in addition to these synthetic fibers, recycled fibers such as rayon or cupra, and natural fibers such as cotton. As the nonwoven fabric, a non-woven fabric obtained by appropriate processing methods such as a spun lace method, a spun bond method, a thermal bond method, a melt-blown method, and a needle punch method can be used.

It is preferable that the second sheet 6 does not include a non-heat fusible fiber, specifically, the above-described cellulose fiber. It is preferable that the second sheet 6 includes only a heat-fusible fiber, specifically, a synthetic fiber. As described in detail later, the second sheet 6 is heat-fused to an upper layer side of the heat-fusible layer 11 of the top-surface sheet 3 in the compressed part 15. Therefore, when a non-heat fusible fiber is included, the second sheet 6 is not easily heat-fused to the heat-fusible layer 11 in the compressed part 15. Consequently, joining strength between the second sheet 6 and the heat-fusible layer 11 may be deteriorated. The heat-fusible fiber of the second sheet 6 and the heat-fusible fiber of the heat-fusible layer 11 are preferably fiber raw materials having substantially the same level of melting point, and particularly preferably the same fiber raw materials.

The second sheet 6 is preferably formed at a lower basis weight and in a lower density than the heat-fusible layer 11. Thus, when the compressed parts 15 as described in detail later, are formed, the second sheet 6 is easily joined to the heat-fusible layer 11, a part of the fibers of the heat-fusible layer 11 enters between fibers of the second sheet 6, and a body fluid easily moves from the heat-fusible layer 11 to the second sheet 6. The basis weight of the second sheet 6 is 13 to 35 g/m$^2$, and preferably 13 to 18 g/m$^2$.

As the second sheet 6, a raw material fiber having hydrophilicity to a body fluid is preferably used. Specifically, a fiber having hydrophilicity imparted by surface-treating a synthetic fiber with a hydrophilizing agent can be used. The second sheet 6 preferably has higher hydrophilicity than the heat-fusible layer 11 of the top-surface sheet 3.

<Compressed Part>

As shown in FIG. 4, a large number of compressed parts 15, 15 . . . obtained by integrally recessing the second sheet 6 and the top-surface sheet 3 toward the skin side are formed on the non-skin side surface of the second sheet 6. The compressed parts 15 are recessed parts formed by compressing from the non-skin side of the second sheet 6 in a state in which the second sheet 6 is laminated on the non-skin side (outer surface side of the heat-fusible layer 11) of the top-surface sheet 3, while heat or ultrasonic wave is applied to melt and solidify the heat-fusible layer 11 and the heat-fusible fiber of the second sheet 6 to retain a compression state. In this compressed part 15, the heat-fusible layer 11 and the second sheet 6 strongly adhesively fixed to each other, and the top-surface sheet 3 and the second sheet 6 are integrated with each other. A laminate of the top-surface sheet 3 and the second sheet 6 is formed to have a flat skin-side surface, and a large number of recessed parts corresponding to the compressed parts 15 . . . are formed on the non-skin side surface.

Since the top-surface sheet 3 and the second sheet 6 are adhesively fixed to each other by the compressed parts 15 in this way, the top-surface sheet 3 and the second sheet 6 are brought into close adhesion with each other without a gap therebetween, and liquid pool is not generated between these layers, a body fluid easily moves from the top-surface sheet 3 to the second sheet 6.

Furthermore, since the compressed parts 15 are formed by compression from the non-skin side of the second sheet 6, the non-heat fusible layer 10 on the skin side is not subjected to process for providing recesses and protrusions in a high temperature state, release of entanglement of fibers due to compression in a high temperature state and breakage of nonwoven fabric accompanying with this can be prevented, and smoothness of the surface can be maintained, and deterioration of a touch or reduction of strength can be prevented.

As shown in FIG. 1, the compressed parts 15 are preferably formed in an intermittent pattern in which a large number of compressed parts 15 are disposed at intervals. In the example showing the drawing, dot-like compressed parts 15 are disposed in a staggered arrangement with a predetermined interval. The compressed parts 15 may be disposed in a regular lattice at a predetermined intervals along the width direction and the longitudinal direction of the sanitary napkin 1.

Furthermore, in the example shown in FIG. 1, the compressed parts 15 are provided over the entire part of the top-surface sheet 3, but they may be provided only on a main region such as a region corresponding to the body fluid discharge portion H, and the like, and may not be provided on the other region. Thus, a body fluid smoothly moves from the top-surface sheet 3 to the second sheet 6 in the region corresponding to the body fluid discharge portion H, and a sheet can be prevented from becoming hard by compression in the other region, and thus a softer touch feeling of cellulose fibers can be further provided The size of each compressed part 15 is preferably 1 to 10 mm, and more preferably 1 to 3 m. When the size is smaller than 1 mm, the joining strength per one section of compressed part 15 between the heat-fusible layer 11 and the second sheet 6 becomes small, and close adhesion between the heat-fusible layer 11 and the second sheet 6 is deteriorated, a body fluid moves more smoothly. On the other hand, when the size is larger than 10 mm, the hardness of the compressed part 15 may be felt more easily to thus deteriorate the feeling of wearing.

The shape of the compressed part 15 is a circular shape in the drawing, but it can be an elliptical shape, a polygonal shape, or the like.

As shown in FIG. 1, the interval B between the adjacent compressed parts 15, 15 is 3 to 15 mm, and preferably 5 to 10 mm. If this interval B is smaller than 3 mm, the compressed parts 15, 15 are too close to each other, causing the top-surface sheet 3 to be hard. On the other hand, if this interval B is larger than 15 mm, the close adhesion between the heat-fusible layer 11 and the second sheet 6 is deteriorated, so that a body fluid is not moved smoothly. The intervals B in the example shown in FIG. 1 are substantially constant along the entire surface, but they may be changed depending on the region. For example, the close adhesion between the heat-fusible layer 11 and the second sheet 6 can be increased in the region corresponding to the body fluid discharge portion H so as to relatively reduce the interval B such that a body fluid moves easily, and the adhesive can be made large so as to maintain the flexible feeling in the other region. Furthermore, around the region corresponding to the body fluid discharge portion H as a center, the intervals B may be gradually increased toward the outer peripheral side of the sanitary napkin 1.

The emboss rate that is a rate of the total area of the large number of the compressed parts 15, 15 . . . to an area of the second sheet 6 is 1 to 20%, and preferably 6 to 15% from the viewpoint that the joining strength between the second sheet 6 and the heat-fusible layer 11 is enhanced to make a body fluid to move more easily, and that deterioration of feel of wearing due to the hardness of the compressed parts 15 is prevented.

The compression depth of each compressed part 15 is to the middle position of the non-heat fusible layer 10 as shown in FIG. 4, and it is preferable that the depth is set such that not a large portion of the non-heat fusible layer 10, and preferably more than half of the thickness is not compressed. Thus, also in the portion provided with compressed parts 15, the skin-side surface of the non-heat fusible layer 10 can sufficiently maintain the flexible feeling. In the compressed parts 15, at the time of compression, the heat-fusible layer 11 and the heat-fusible fiber of the second sheet 6 in the bottom portion are melted and solidified, so that the shape of the predetermined recess is maintained. Furthermore, a part of the melted heat-fusible fiber flows into between fibers of the non-heat fusible layer 10 in the bottom portions of the compressed parts 15 and is solidified, so that the joining strength between the heat-fusible layer 11 and the non-heat fusible layer 10 can be enhanced.

By providing the compressed parts 15, in the non-heat fusible layer 10, a part of the non-skin side is compressed, and the fiber density becomes higher. Therefore, due to the capillary action accompanying the density difference of the fibers, the body fluid absorbed by the non-heat fusible layer 10 is easily drawn into the compressed part 15. The body fluid drawn into the compressed part 15 is easily transferred to the second sheet 6 by entanglement of the fibers between the layers and the density difference of the fibers caused by the compression process. Therefore, it is advantageous that by providing the compressed parts 15, liquid remaining on the surface in the non-heat fusible layer 10 becomes small, and the sticky feeling can be reduced, and the rash due to steaming can also be prevented.

<Manufacturing Method>

Next, a method for manufacturing the sanitary napkin 1 will be described. Herein, a method for forming compressed parts 15, as a feature of the present invention, will be described in detail. The other process is the same as the manufacturing method of general sanitary napkins.

Figure 6:
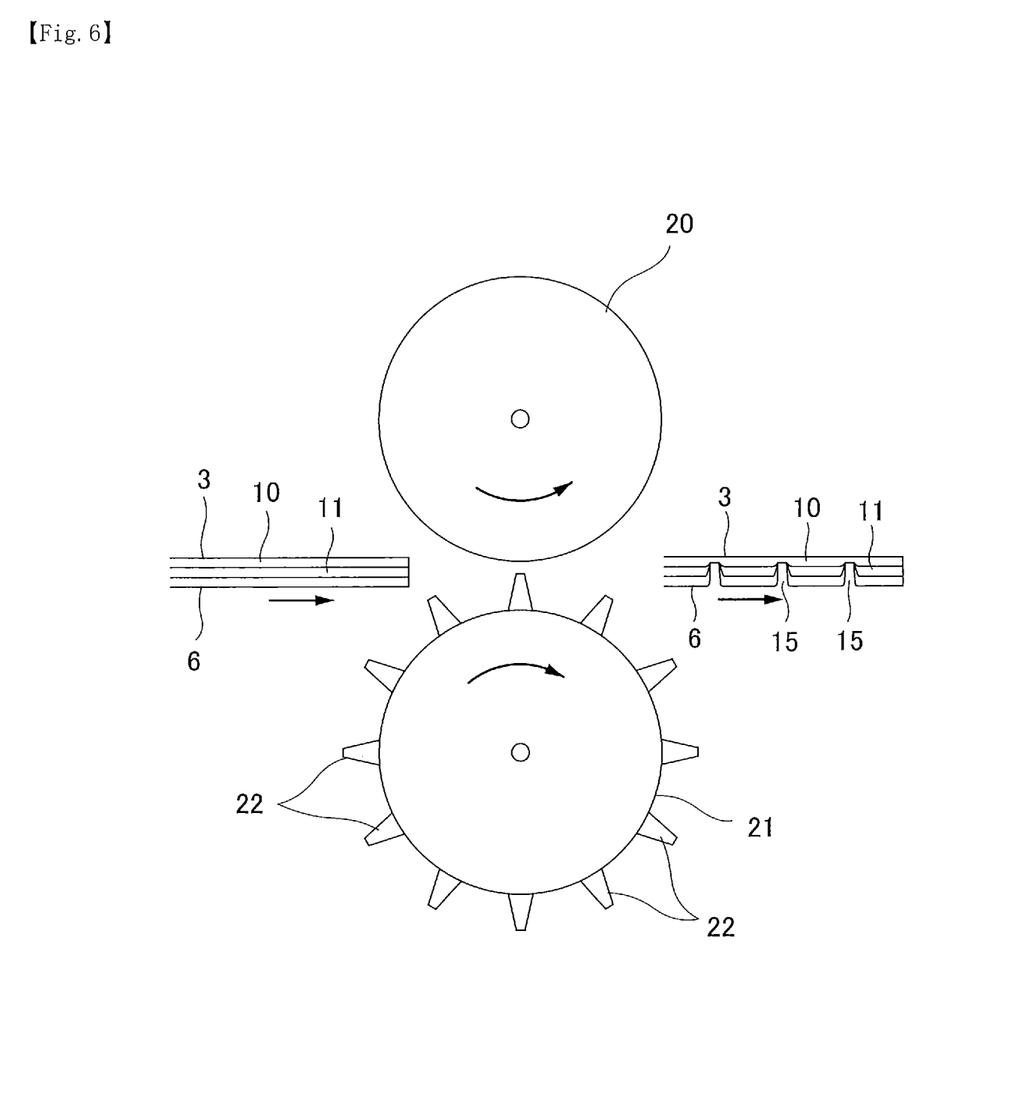
FIG. 6 is a sectional view showing a first manufacturing method.

A first embodiment, as shown in FIG. 6, can include a method of allowing a laminate of a top-surface sheet 3 and a second sheet 6 to pass between a flat roll 20 having a flat surface and not being heated, and a convex roll 21 having a surface formed with a large number of protrusions 22, 22 . . . corresponding to the compressed parts 15 . . . and being heated at least at the time of compression, and thereby heat-fusing and joining the second sheet 6 and the heat-fusible fiber of the heat-fusible layer 11 to each other while forming the compressed parts 15 . . . .

Thus, a laminate of the top-surface sheet 3 and the second sheet 6 is obtained in which the skin-side surface of the top-surface sheet 3 is flat and is excellent in a touch feeling, while the heat-fusible layer 11 of the top-surface sheet 3 and the second sheet 6 are strongly joined in the compressed part 15. Furthermore, since a flat roll 20 is used as the roll facing the non-heat fusible layer 10 of the top-surface sheet 3, since a partial pressing force from a non-heat fusible layer 10 side does not act on, and compression is performed in a state in which the flat roll 20 is not heated and only the convex roll 21 is heated, it is possible to prevent nonwoven fabric and the like from being broken by release of entanglement of fibers of the non-heat fusible layer 10 by heating or compression processing at the time of compression, smoothness of the surface of the non-heat fusible layer 10 can be maintained, and deterioration of the touch and deterioration of the strength can be prevented.

Figure 7:
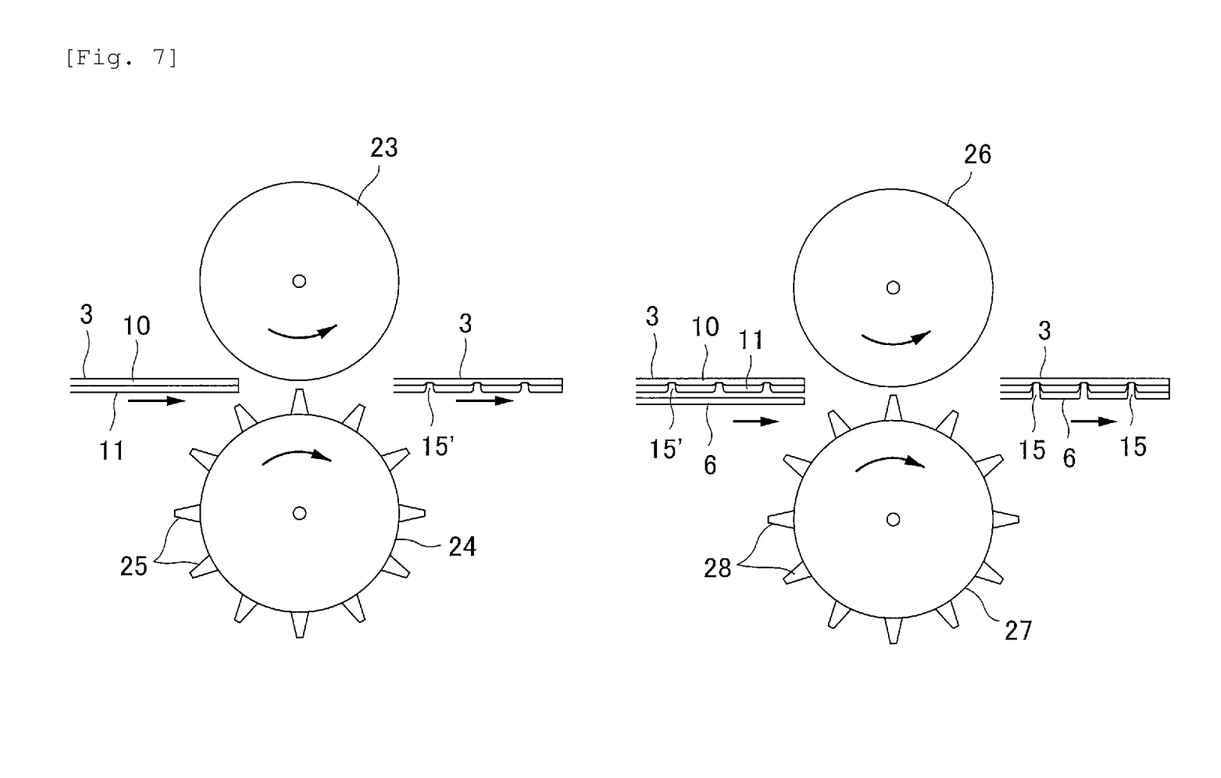
FIG. 7 is a sectional view showing a second manufacturing method.

Next, a second embodiment provides a method, as shown in FIG. 7, the method includes allowing a top-surface sheet 3 having a two-layer structure including a non-heat fusible layer 10 and a heat-fusible layer 11 to pass between a flat roll 23 having a flat surface and not being heated and convex roll 24 having a surface formed with a large number of protrusions 25, 25 . . . and being heated at least at the time of compression to form intermediate compressed parts 15', 15' . . . by integrally recessing the heat-fusible layer 11 and the non-heat fusible layer 10 toward the skin side, and then to pass between a second flat roll 26 having a flat surface and not being heated, and a second convex roll 27 having a surface formed with a large number of protrusions 28, 28 . . . corresponding to the compressed parts 15 . . . and being heated at least at the time of compression, thereby heat-fusing and joining the second sheet 6 and the heat-fusible fiber of the heat-fusible layer 11 while forming the compressed parts 15 . . . .

In the second embodiment, by forming the intermediate compressed parts 15' . . . on the top-surface sheet 3 in advance, joining strength between the non-heat fusible layer 10 and the heat-fusible layer 11 is enhanced. Thereafter, compressed parts 15 are formed in a state in which the top-surface sheet 3 and the second sheet 6 are laminated. This compressed parts 15 . . . may be provided to the recessed parts of the intermediate compressed parts 15' . . . , or may be provided to sites other than the intermediate compressed parts 15' . . . .

REFERENCE SIGNS LIST

1: Sanitary napkin
2: Back-surface sheet
3: Top-surface sheet
4: Absorber
5: Encapsulating sheet
6: Second sheet
7: Side nonwoven fabric
8: Thread-like elastic stretchable member
10: Non-heat fusible layer
11: Heat-fusible layer
12: Opening
13: Vertical stripe
14: Horizontal stripe
15: Compressed part
15': Intermediate compressed part
20: Flat roll
21: Convex roll
22: Protrusion
23: Flat roll
24: Convex roll
25: Protrusion
26: Second flat roll
27: Second convex roll
28: Protrusion

The invention claimed is:

1. A method for manufacturing an absorbent article, the absorbent article comprising a top-surface sheet, a back-surface sheet, and an absorber interposed between the top-surface sheet and the back-surface sheet,
wherein the top-surface sheet includes a non-heat fusible layer arranged on a skin side and made of a nonwoven fabric made of 100% by weight of cotton fiber and a heat-fusible layer arranged on a non-skin side and made of a heat-fusible fiber,
a second sheet made of a heat-fusible fiber is arranged on the non-skin side of the top-surface sheet,
the top-surface sheet is formed to have a flat skin-side surface, and a large number of compressed parts are formed on a non-skin side surface of the second sheet by integrally recessing the second sheet and the top-surface sheet toward the skin side by compression from the non-skin side of the second sheet,
the method comprising:
allowing a laminate of the top-surface sheet and the second sheet to pass between a flat roll and a convex roll, the flat roll having a flat surface and not being heated, and the convex roll having a surface formed with a large number of protrusions corresponding to the compressed parts and being heated at least at a time of compression, thereby heat-fusing and joining the second sheet and the heat-fusible fiber of the heat-fusible layer while forming the compressed parts.

2. A method for manufacturing an absorbent article, the absorbent article comprising a top-surface sheet, a back-surface sheet, and an absorber interposed between the top-surface sheet and the back-surface sheet,
wherein the top-surface sheet includes a non-heat fusible layer arranged on a skin side and made of a nonwoven fabric made of 100% by weight of cotton fiber and a heat-fusible layer arranged on a non-skin side and made of a heat-fusible fiber,
a second sheet made of a heat-fusible fiber is arranged on the non-skin side of the top-surface sheet,
the top-surface sheet is formed to have a flat skin-side surface, and a large number of compressed parts are formed on a non-skin side surface of the second sheet by integrally recessing the second sheet and the top-surface sheet toward the skin side by compression from the non-skin side of the second sheet,
the method comprising:
allowing the top-surface sheet to pass between a flat roll and a convex roll, the flat roll having a flat surface and not being heated, and the convex roll having a surface formed with a large number of protrusions and being heated at least at a time of compression to form a large number of intermediate compressed parts in a non-skin side surface of the top-surface sheet by integrally recessing the heat-fusible layer and the non-heat fusible layer toward a skin side, and
then in a state in which the second sheet is laminated on the non-skin side of the top-surface sheet, allowing the top-surface sheet to pass between a second flat roll and a second convex roll, the second flat roll having a flat surface and not being heated, and the second convex roll having a surface formed with a large number of protrusions corresponding to the compressed parts and being heated at least at compression time, thereby heat-fusing and joining the second sheet and the heat-fusible fiber of the heat-fusible layer while forming the compressed parts.

3. The method for manufacturing the absorbent article according to claim 1, wherein a large number of the compressed parts are formed in an intermittent pattern in which the compressed parts are disposed at intervals.

4. The method for manufacturing the absorbent article according to claim 2, wherein a large number of the compressed parts are formed in an intermittent pattern in which the compressed parts are disposed at intervals.

* * * * *